(12) United States Patent
Molteni et al.

(10) Patent No.: US 7,077,567 B1
(45) Date of Patent: Jul. 18, 2006

(54) X-RAY TUBEHEAD HOUSING WITH SLANT-ANGLE PARTITION

(75) Inventors: Roberto Molteni, Arlington Heights, IL (US); Donald Walker, Mundelein, IL (US)

(73) Assignee: Gendex Corporation, Washington, DC (US)

( * ) Notice: Subject to any disclaimer, the term of this patent is extended or adjusted under 35 U.S.C. 154(b) by 0 days.

(21) Appl. No.: 11/103,053

(22) Filed: Apr. 11, 2005

(51) Int. Cl.
*H05G 1/02* (2006.01)

(52) U.S. Cl. ..................................... 378/193
(58) Field of Classification Search ............... 378/119, 378/121, 193, 196, 203
See application file for complete search history.

(56) References Cited

U.S. PATENT DOCUMENTS

| | | | | |
|---|---|---|---|---|
| 3,473,028 A * | 10/1969 | Curry | .......................... | 378/193 |
| 4,741,007 A | 4/1988 | Virta et al. | .................... | 378/39 |
| 4,795,654 A | 1/1989 | Teliki | .......................... | 428/635 |
| 4,811,372 A | 3/1989 | Doebert et al. | ................ | 378/39 |
| 4,840,471 A | 6/1989 | Mitani et al. | ................ | 359/722 |
| 4,847,881 A | 7/1989 | Huebeck | ....................... | 378/38 |
| 4,852,134 A | 7/1989 | Kinanen et al. | .............. | 378/38 |
| 6,644,853 B1 | 11/2003 | Kantor et al. | ................ | 378/203 |
| 6,775,353 B1 * | 8/2004 | Thandiackal et al. | ........ | 378/119 |

* cited by examiner

*Primary Examiner*—Courtney Thomas
(74) *Attorney, Agent, or Firm*—McNees Wallace & Nurick LLC

(57) ABSTRACT

A container to secure an x-ray source is provided. The container includes a base and a cover each having an inside surface. The base and cover are assembled together forming a fluid tight chamber defined by the inside surfaces of the base and cover to secure x-ray source components to positions along the inside surface of the base. A plurality of these positions are machinable to provide a precision arrangement of at least a portion of the x-ray source components and at least one fluid tight seal between x-ray source components and the base. During fabrication of the base, each position of the inside surface required to provide a precise arrangement of at least a portion of the x-ray source components and at least one fluid tight seal between the x-ray source components and the base being accessible from exterior of the base by a substantially straight tool.

23 Claims, 3 Drawing Sheets

US 7,077,567 B1

X-RAY TUBEHEAD HOUSING WITH SLANT-ANGLE PARTITION

FIELD OF THE INVENTION

The present invention is directed to a container for use with x-ray equipment, and more particularly, is directed to a container that is used in dental x-ray equipment to house an x-ray source.

BACKGROUND OF THE INVENTION

X-ray equipment is commonly used in the dental industry to assist dental professionals. Typically, the x-ray source and associated components are enclosed within a suitable high voltage housing, referred to as a tubehead housing, which contains a high-dielectric insulating fluid, such as dielectric oil, that also operates as a coolant. The housing may also provide shielding of the unwanted radiation outside a designated output window formed in the housing. It is important that the assembled tubehead housing provides a fluid tight seal to prevent inadvertant leakage of the dielectric oil from the tubehead housing.

Typically, the tubehead housing resembles a rectangle, i.e., having adjacent surfaces disposed at right angles to each other. For ease of assembly and to minimize the opportunity for leakage, it is preferred that the tubehead housing is comprised of only two pieces, such as a box structure and a lid. However, to complicate matters, portions of the tubehead housing surface require precision machining for such reasons as alignment between certain components within the tubehead housing and providing a fluid tight seal between tubehead housing components and the tubehead housing. Currently, tubehead housing configurations require precision machining to be performed on each portion of the tubehead housing, which significantly increases manufacturing costs. Additionally, such precision is further complicated in that the precision machining for at least one portion of the tubehead housing cannot be performed by a standard machining tool, such as an end mill, which requires "straight on" access. In other words, a straight cutting tool that can only be advanced in a straight line is incapable of machining all the required surfaces of at least one of the tubehead housing portions. The additional nonstandard precision machining techniques required to machine these remaining surfaces further increase manufacturing costs. Finally, once machining to the tubehead housing has been completed and the internal components installed, current tubehead housing configurations fail to provide sufficient accessibility to the internal components.

What is needed is a tubehead housing construction for securing x-ray components therein that is easy to manufacture, including subsequent precision machining, and having ease of accessibility to internal components when the tubehead housing is disassembled.

SUMMARY OF THE INVENTION

The present invention relates to a container to secure an x-ray source including a base having an inside surface and a cover having an inside surface and being detachably connected to the base. The base and the cover are configured and disposed to form a fluid tight chamber defined by the inside surfaces of the base and cover, the inside surface of the base comprising a plurality of attachment positions for x-ray source components, the plurality of attachment positions being precision machined into the inside surface of the base. During fabrication of the base, each attachment position of the plurality of attachment positions being accessible from exterior of the base by a substantially straight tool.

The present invention also relates to a method of manufacturing a container for an x-ray source including: forming a base having an inside surface; forming a cover having an inside surface and being detachably connectable to the base, the base and the cover being configured and disposed to form a fluid tight chamber defined by the inside surface of the base and cover; and precision machining a plurality of attachment positions for x-ray source components into the inside surface of the base by a substantially straight tool.

The present invention further relates to a container to secure an x-ray source including a base having an opening, an inside surface and an outside surface, the outside surface including a substantially planar portion opposite the opening. A cover has an opening, an inside surface and an outside surface opposite the opening, the outside surface including a substantially planar portion, the cover being detachably connectable to the base. The base and the cover are configured and disposed to form a fluid tight chamber defined by the inside surfaces of the base and cover to secure x-ray source components therein. A junction along the openings of the base and cover is nonparallel to the substantially planar portions of the outer surfaces of the base and cover.

An advantage of the present invention is that it can be constructed from a casting.

A further advantage of the present invention is that only the base of the tubehead housing requires precise machining.

A still further advantage of the present invention is that machining of the base of the tubehead housing can be achieved by a substantially straight tool directed from exterior of the tubehead housing.

An additional advantage of the present invention is that when the tubehead housing is assembled or disassembled, x-ray components are readily accessible.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
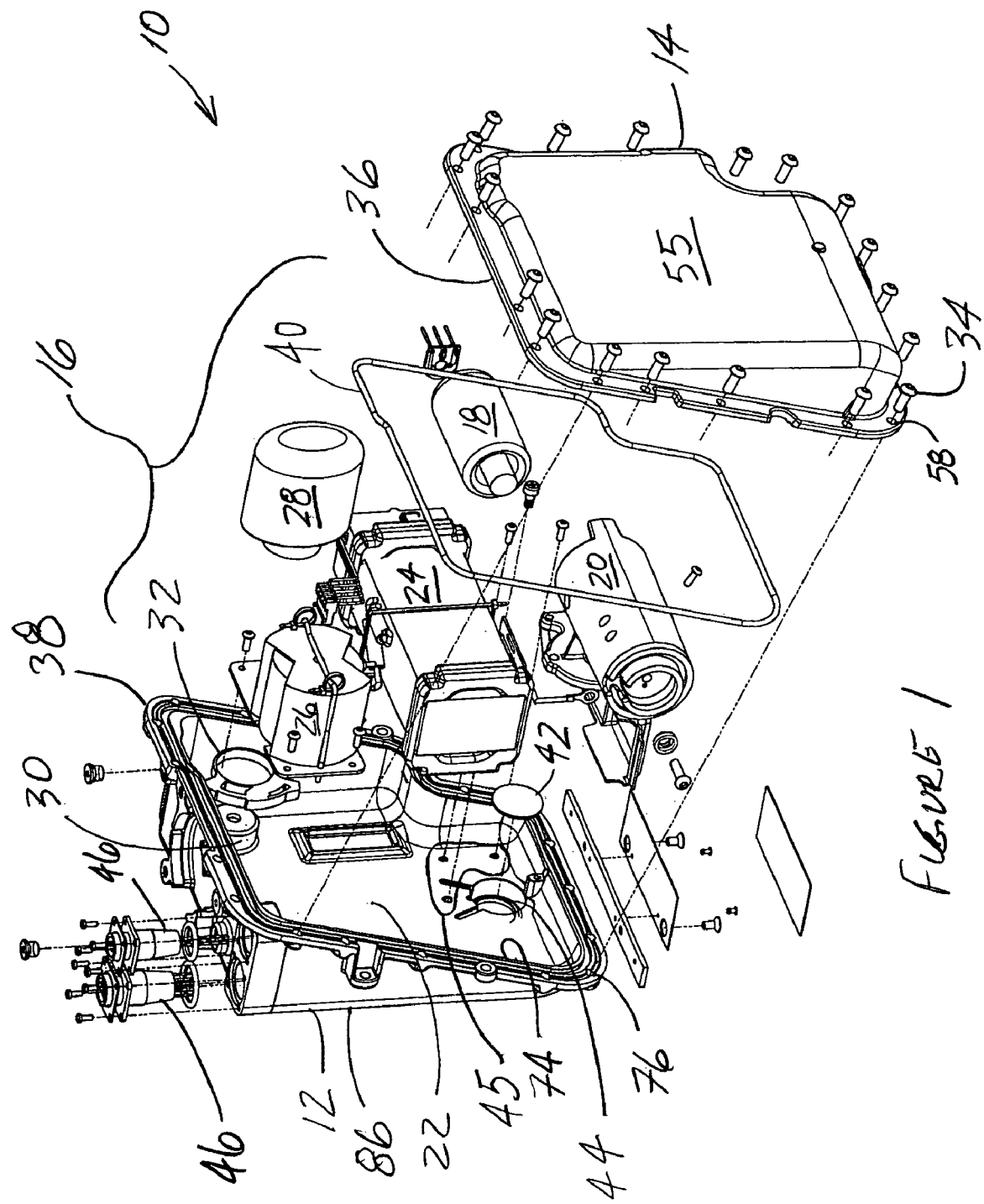
FIG. 1 is an exploded perspective view x-ray components that are secured inside of a tubehead housing of the present invention.
Figure 4:
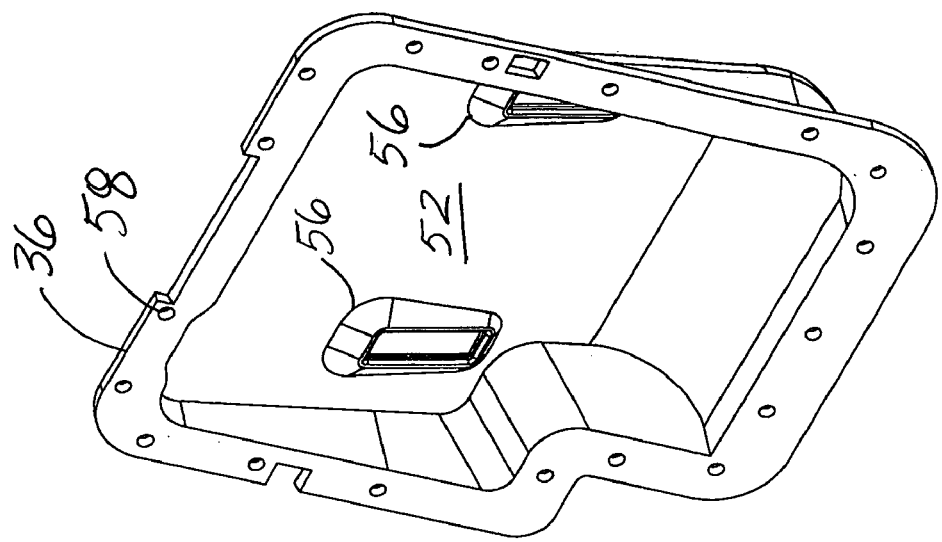
FIGS. 2–4 show different views of a cove of a tubehead housing of the present invention.
Figure 5:
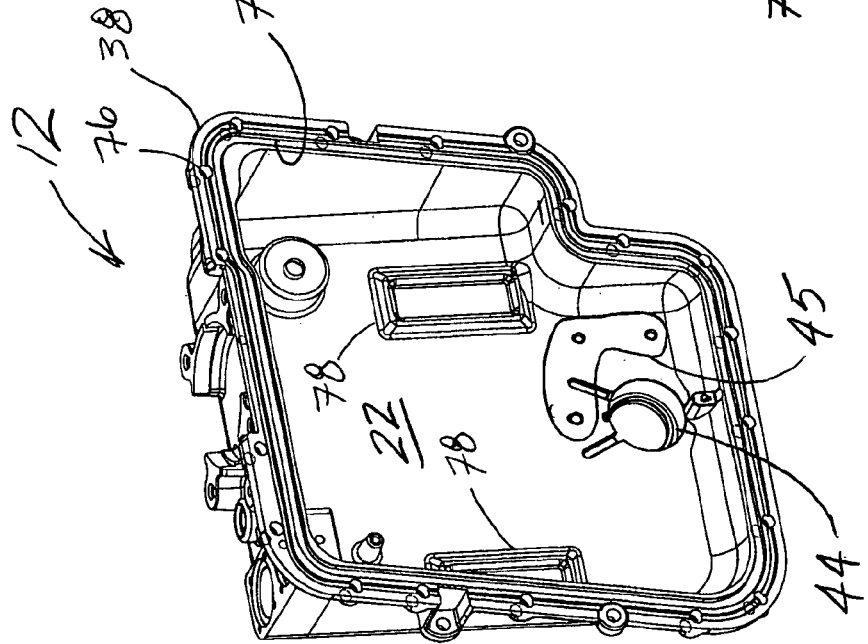

One embodiment of a tubehead housing 10 of the present invention is depicted in FIG. 1 Preferably, the tubehead housing 10 includes a base 12 and a cove 14 that secure x-ray system components 16 therebetween. For purposes of orientation, a substantially planar surface 55 of the cover 14 is referred to herein as rear surface 55, and an opposed substantially planar surface of the base 12 is referred to herein as a front surface 86. The x-ray components 16, include an x-ray tube 18 that is secured with a tube holder 20, a radiation filter 42, a high voltage multiplier 24, and a transformer 26. Electrical power provided by an electrical power source is supplied to the x-ray components 16 via a pair of electrical connectors 46. Both the x-ray components 16 and the electrical connectors 46 are secured to the base 12, although the high voltage multiplier 24 is more accurately sandwiched between extensions 78, 56 (see FIGS. 4 and 5) formed in the respective base 12 and cover 14. Once the x-ray components 16 are secured to the base 12, a peripheral flange 38 of the base 12 and a peripheral flange 36 of the cover 14 are brought together with a gasket 40 interposed between the flanges 36, 38. Fasteners 34 sufficiently compress the gasket 40 between the flanges 36, 38 to achieve a fluid tight seal therebetween. A dielectric fluid (not shown) is then pumped inside the tubehead housing 10, with a bellows 28 that is secured to a port 30 by a clamp 32. The bellows 28 compensates for volume changes inside the tubehead housing 10, primarily due to temperature changes and differing coefficients of volumetric expansion/contraction between the dielectric fluid, tubehead housing 10 and x-ray components 16.

As will be discussed in further detailed below, the construction of the tubehead housing 10, notably the angled portion defined by the flanges 36, 38 of the respective cover 14 and base 12, permits a significant reduction in costs associated with the manufacturing of the tubehead housing 10, as well as improved accessibility of the installed x-ray system components 16.

Figure 3:
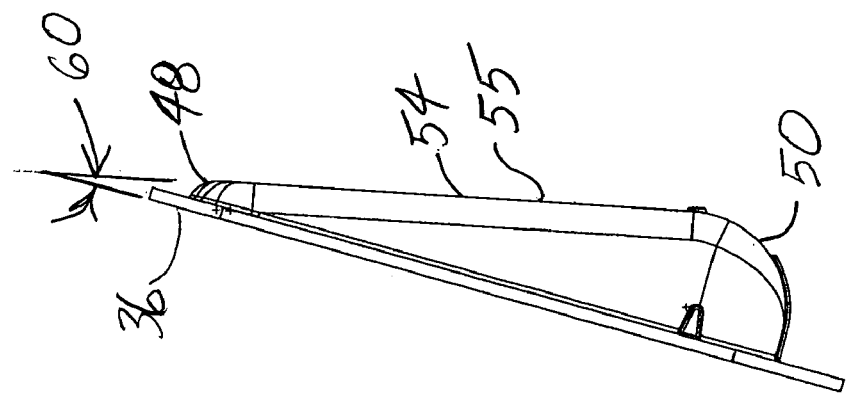
Figure 2:
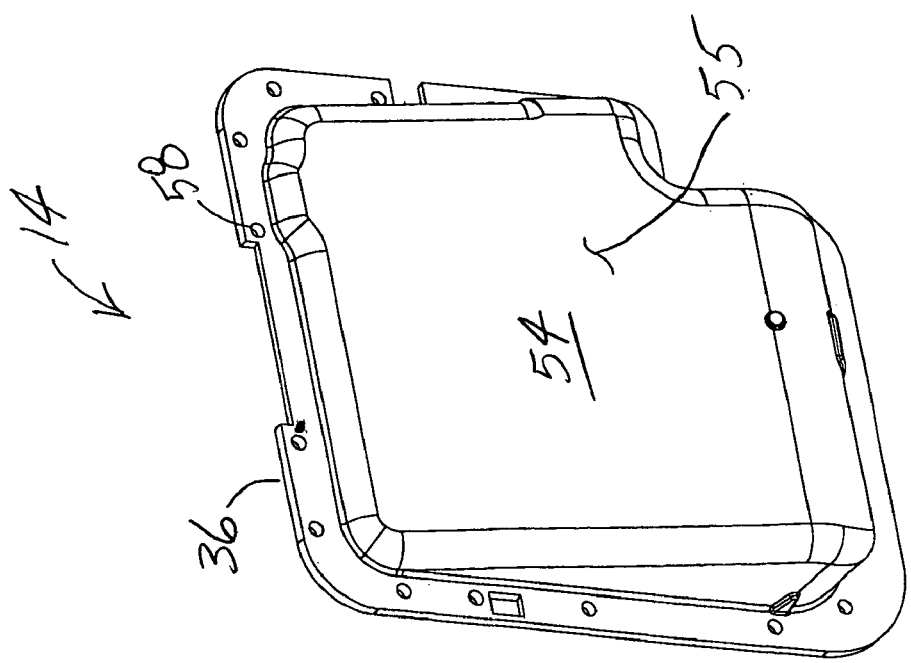
Figure 7:
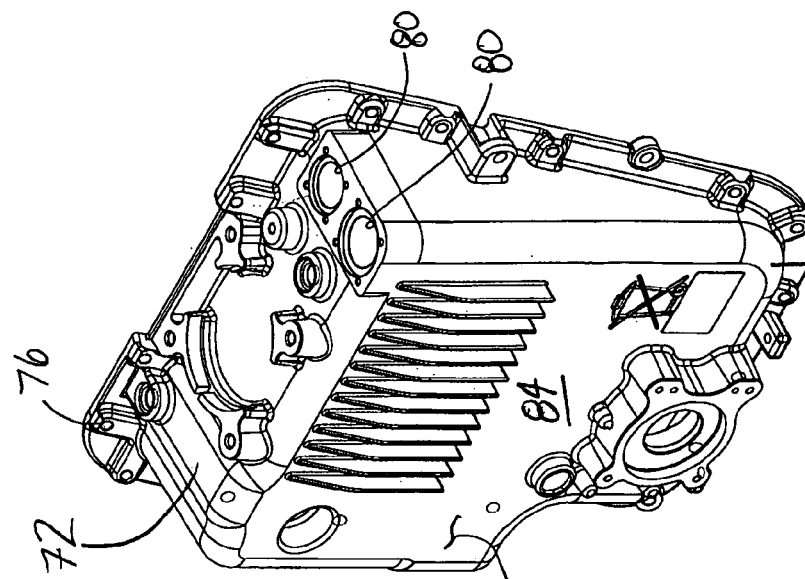
FIGS. 5–7 show different views of a base of a tubehead housing of the present invention.

Referring to FIGS. 1–4, the cove 14 preferably includes a narrow end 48 extending to a wide end 50, cover 14 substantially defining a wedge shape. The cover 14 has an outside surface 54 and an inside surface 52 with a pair of extensions 56 extending away from the inside surface 52 to help secure the high voltage multiplier 24 (FIG. 1). Surrounding the inside surface 52 and separating the inside surface 52 from the outside surface 54 is peripheral flange 36 that contacts the peripheral flange 38 of the base 12 when assembled. The gasket 40 located between flanges 36, 38 is positioned such that a compressing gasket 40 between flanges 36, 38 achieves a fluid tight seal. Preferably, flange 36 is substantially planar, as shown in FIG. 3, and defines an acute angle 60 with the rear surface 55 of the cover 14. Specifically, the narrow end 48 has a first height in extending between the flange 36 and rear surface 55 and the wide end 50 has a second height greater than the first height in extending between the flange 36 and rear surface 55. In a preferred embodiment, the cover 14 is constructed of metal, and more preferably cast metal, although other suitable materials can be used. Preferably, angle 60 is sized so that flange 36 is neither perpendicular nor parallel to either of the inside or outside surfaces 55, 55 or the surface adjacent the wide end 50.

Additionally, a preferred embodiment of the cover 14 does not require subsequent precision machining operations after forming. The term "subsequent precision machining operations" is not intended to include normal cleanup operations, such s removing casting edge irregularities formed at the junction of parting dies, which may be quickly performed by passing a grinding wheel along a rough edge of the cover 14. However, subsequent precision machining is intended to refer to machining operations considered critical to component alignment or fit, requiring a sufficiently high degree of precision that the amount of material removed must be closely monitored, and cannot typically be performed manually without tooling. In the above example, it certainly is not crucial to remove edge casting irregularities extending radially outwardly along the outer periphery of the flange 36 (along the die partition line) other than what is required to break sharp edges.

Figure 6:
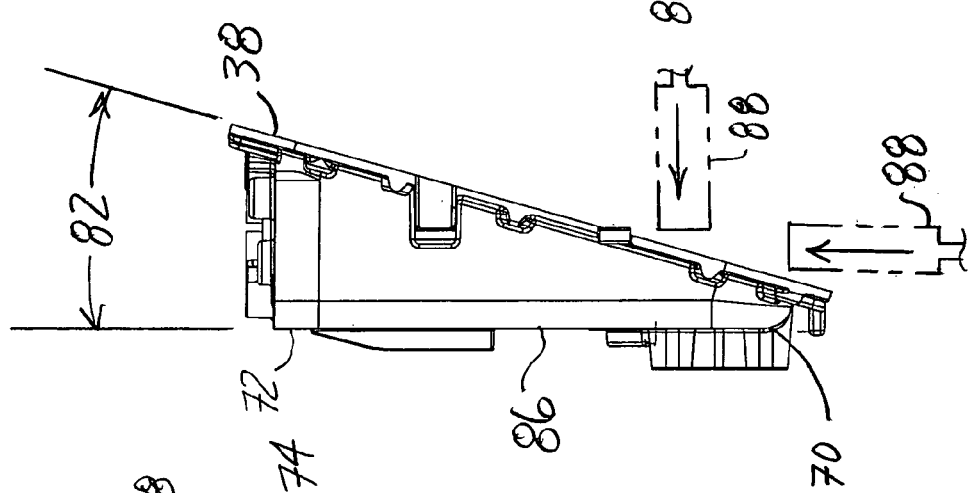

Referring to FIGS. 1 and 5–7, base 12 preferably includes a narrow end 70 extending to a wide end 72, base 12 substantially defining a wedge shape. The base 12 has an outside surface 84 and an inside surface 22 with a pair of extensions 78 extending away from the inside surface 22 to help secure the high voltage regulator 24 (FIG. 1). Surrounding the inside surface 22 and separating the inside surface 22 from the outside surface 84 is peripheral flange 38, which contacts the peripheral flange 36 of the cover 14. The gasket 40 located between flanges 36, 38 is positioned and partially embedded in a peripheral groove 74 formed in flange 38 such that compressing gasket 40 between flanges 36, 38 achieves a fluid tight seal. The inside surfaces 22, 52 of the assembled cover 14 and base 12, respectively, form a chamber configured to contain the x-ray components 16 therein. Preferably, other than the groove 74, flange 38 is substantially planar, as shown in FIG. 6, and defines an acute angle 82 with the front surface 86 of the cover 14. In a preferred embodiment, the base 12 is constructed of metal, and more preferably cast metal, although other suitable materials can be used. Preferably, angle 82 is sized so that the flange 38 is neither parallel nor perpendicular to either of the front surface 86 or the surface adjacent wide end 72.

Contrary to the cover 14, which does not require subsequent precision machining, the base 12 includes several positions along the inside surface 22 and the outside surface 84 that require subsequent precision machining. For example, one position typically requiring such machining is a recess 44 disposed opposite front surface 86 to ensure the radiation filter 42 forms a fluid tight seal with the inside surface 22. Adjacent to the recess 44, another position is an aperture pattern 45 which secures the x-ray tube holder 20, since alignment between the x-ray tube holder 20 and the base 12 is critical. In other words, not only is the location of the apertures of the aperture pattern 45 with respect to each other and with respect to the base 12 of critical importance, but also, the planar alignment of the apertures of the aperture pattern 45 with respect to locating points along the outside surface 84. Additionally, other positions along the inside surface 22 include the aperture patterns 80 disposed along the wide end 72. Although the locations of the aperture patterns 80 with respect to each other or with respect to the base 12 may not be critical, each of the aperture patterns 80 require precision machining along the inside surface 22 to ensure a fluid tight seal between the electrical connectors 46 and their corresponding aperture pattern 80.

To minimize the dimensions of the tubehead housing 10 in one embodiment, the electrical connectors 46, and therefore the corresponding aperture patterns 80, are disposed in the base 12 along the wide end 72. In this arrangement, the aperture patterns 80 are not only separated from the recess 44 and adjacent aperture pattern 45, but are formed in different orientations, as the wide end 72 and the front surface 86 are substantially perpendicular. Such an arrangement in prior art tubehead housing constructions would present machining access problems in that a straight tool 88 (FIG. 6) could not access all the different positions requiring precision machining. However, due to the novel angled flange 38 construction, it is appreciated that the portion of the flange 38 adjacent to the narrow end 70 is disposed so that a straight tool 88 can directly access aperture patterns 80 from exterior of the base 12. Similarly, the straight tool 88 can directly access the recess 44 and the aperture pattern 45 from exterior of the base 12. This ability to directly access all of the inside surface positions from exterior of the base 12 by the straight tool 88 significantly reduces manufacturing costs.

By virtue of the angle 82 between the flange 38 and the front surface 86 of the base 12 being substantially equal to the angle 60 between the flange 36 and the rear surface 55 of the cover 14, forming alternate interior angles when the base 12 is assembled to the cover 14, the front surface 86 and the rear surface 55 are substantially parallel. While preferred, it is not necessary that the angles 60, 82 be substantially equal, or that the front surface 86 and the rear surface 55 be substantially parallel. It is to be understood that the angles 60, 82 can range significantly in magnitude to accommodate the components inserted between the assembled base 12 and cover 14. However, in a preferred embodiment the angles 60, 82 range from about 12 to about 40 degrees.

It is also appreciated by those skilled in the art that having the angled flange 38 in the base 12 improves accessibility of x-ray components 16 secured to the inside surface 22. Although it is preferred that the flanges 36, 38 of respective cover 14 and base 12 are planar, it is not required, so long as the profiles correspond to each other and define an overall profile that is not parallel to the respective front or rear surfaces. Further it is to be understood that the acute angles 60, 82 can be compound angles. That is, neither wide ends 72, 50 nor narrow ends 70, 48 of respective base 12 and cover 14 are required to be of uniform width.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A container to secure an x-ray source comprising:
    a base having an inside surface;
    a cover having an inside surface and being detachably connected to the base;
    the base and the cover being configured and disposed to form a fluid tight chamber defined by the inside surfaces of the base and cover, the inside surface of the base comprising a plurality of attachment positions for x-ray source components, the plurality of attachment positions being precision machined into at least two non-parallel portions of the inside surface of the base; and
    wherein prior to assembly of the base and cover, each attachment position of the plurality of attachment positions being accessible from exterior of the base by a substantially straight tool.

2. The container of claim 1 wherein the base and cover each comprise a peripheral flange, the peripheral flanges being brought together to achieve the fluid tight chamber.

3. The container of claim 2 wherein a gasket is interposed between the peripheral flanges.

4. The container of claim 3 wherein fasteners bring the peripheral flanges together.

5. The container of claim 2 wherein the peripheral flanges are substantially planar.

6. The container of claim 2 wherein the peripheral flange of the base forms an angle with an outside surface of the base opposite the peripheral flange.

7. The container of claim 6 wherein the angle is an acute angle.

8. The container of claim 7 wherein the angle is between about 12 and about 40 degrees.

9. The container of claim 8 wherein the angle is a compound angle.

10. The container of claim 2 wherein the peripheral flange of the cover forms an angle with an outside surface of the cover opposite the peripheral flange.

11. The container of claim 10 wherein the angle is an acute angle.

12. The container of claim 11 wherein the angle is between about 12 and about 40 degrees.

13. The container of claim 12 wherein the angle is a compound angle.

14. A method of manufacturing a container for an x-ray source comprising:
    forming a base having an inside surface, the inside surface having at least two non-parallel surface portions;
    forming a cover having an inside surface and being detachably connectable to the base, the base and the cover being configured and disposed to form a fluid tight chamber defined by the inside surfaces of the base and cover; and
    precision machining a plurality of attachment positions for x-ray source components into the inside surface of the base by a substantially straight tool, wherein at least one attachment position being machined into at least two non-parallel surface portions of the at least two non-parallel surface portions.

15. The method of claim 14 wherein the step of forming a base includes the step of forming a peripheral flange, and the step of forming a cover includes the step of forming a peripheral flange, the peripheral flange being brought together to achieve the fluid tight chamber.

16. The method of claim 15 wherein the base peripheral flange and the cover peripheral flange are each substantially planar, the base peripheral flange forming an angle with an outside surface of the base, the cover peripheral flange forming an angle with an outside surface of the cover.

17. The method of claim 16 wherein the angles are acute angles.

18. The method of claim 17 wherein the angles are between about 12 and about 40 degrees.

19. A container to secure an x-ray source comprising:
    a base having an opening, an inside surface and an outside surface, the outside surface including a substantially planar portion opposite the opening;
    a cover having an opening, an inside surface and an outside surface, the outside surface including a substantially planar portion opposite the opening, the cover being detachably connected to the base;
    the base and the cover being configured and disposed to form a fluid tight chamber defined by the inside surfaces of the base and cover to secure x-ray source components therein; and
    wherein a junction along the openings of the base and cover is nonparallel to the substantially planar portions of the outside surfaces of the base and cover.

20. The container of claim 19 wherein the substantially planar portions of the outside surfaces of the base and cover are substantially parallel.

21. The container of claim 19 wherein the junction of the base and cover and at least one of the substantially planar portions of the outside surfaces of the base and cover defines an acute angle.

22. The container of claim 21 wherein the angle is between about 12 and about 40 degrees.

23. The container of claim 22 wherein the angle is a compound angle.

* * * * *

UNITED STATES PATENT AND TRADEMARK OFFICE
CERTIFICATE OF CORRECTION

PATENT NO. : 7,077,567 B1  Page 1 of 1
APPLICATION NO. : 11/103053
DATED : July 18, 2006
INVENTOR(S) : Molteni et al.

It is certified that error appears in the above-identified patent and that said Letters Patent is hereby corrected as shown below:

In column 2, line 6, "surface" should be -- surfaces --,
In column 2, line 56, "cove" should be -- cover --,
In column 3, line 16, "detailed" should be -- detail --,
In column 3, line 22, "cove" should be -- cover --.

Signed and Sealed this

Third Day of October, 2006

JON W. DUDAS
*Director of the United States Patent and Trademark Office*